United States Patent [19]

Huebner

[11] Patent Number: 5,665,087
[45] Date of Patent: Sep. 9, 1997

[54] METHOD AND SCREW FOR REPAIR OF OLECRANON FRACTURES

[76] Inventor: Randall J. Huebner, 18560 SW. Hart Rd., Aloha, Oreg. 97005

[21] Appl. No.: 622,368

[22] Filed: Mar. 26, 1996

[51] Int. Cl.⁶ .................................................. A61B 17/72
[52] U.S. Cl. ........................... 606/65; 606/67; 606/62; 606/72
[58] Field of Search .......................... 606/65, 60, 62, 606/67, 72, 73

[56] References Cited

U.S. PATENT DOCUMENTS

| | | |
|---|---|---|
| 2,270,188 | 1/1942 | Longfellow . |
| 2,631,584 | 3/1953 | Purificato . |
| 3,716,050 | 2/1973 | Johnston . |
| 3,741,205 | 6/1973 | Markolf et al. . |
| 3,763,855 | 10/1973 | McAtee . |
| 3,990,438 | 11/1976 | Pritchard . |
| 4,463,753 | 8/1984 | Gustilo ..................... 606/62 |
| 5,100,405 | 3/1992 | McLaren . |
| 5,375,956 | 12/1994 | Pennig . |
| 5,562,672 | 10/1996 | Huebner et al. ............. 606/73 |

OTHER PUBLICATIONS

"Current Concepts in the Treatment of Fractures of the Radial Head, the Olecranon, and the Coronoid," B.F. Morrey, *The Journal of Bone and Joint Surgery*, vol. 77-A, No. 2, pp. 316-326.

"Treatment of Nonunion of Olecranon Fractures," Panayiotis J. Papageopoulos and Bernard F. Morrey, *The Journal of Bone and Joint Surgery*, vol. 76-B, No. 4, pp. 627-635.

Fractures of the Olecranon/Radial Head, *Practical Fracture Treatment Third Edition*, p. 147.

Zimmer Instruments and Appliances for Orthopedic Surgery (journal of bone and joint surgery, vol. 37A, p. 5 Jul. 1955.

*Primary Examiner*—Michael Buiz
*Assistant Examiner*—Daphna Shai
*Attorney, Agent, or Firm*—Kolisch, Hartwell, Dickinson, McCormack & Heuser

[57] ABSTRACT

A method for repairing fractures of the olecranon including creating a hole in the proximal end of the ulna, where the hole extends from the proximal end of the ulna to the fracture to define a first region, and from the fracture to the proximal end of the medullary canal to define a second region. A screw is selected having a cancellous section and a medullary section extending from the cancellous section. The cancellous section includes a threaded region adjacent the medullary section and the medullary section is adapted to fit into the medullary canal of the ulna. The medullary section is installed into the hole up to the threaded region and the screw is then rotated to drive the threaded region into the hole until the threaded region engages the cancellous bone surrounding the hole in the second region and the medullary section extends substantially into the medullary canal.

16 Claims, 1 Drawing Sheet

METHOD AND SCREW FOR REPAIR OF OLECRANON FRACTURES

FIELD OF THE INVENTION

The present invention relates generally to repair of bone fractures. More particularly, it is directed to a method and apparatus for repairing fractures of the olecranon.

BACKGROUND OF THE INVENTION

The elbow is the joint between the humerus in the upper arm and the ulna and radius in the forearm. The joint between the ulna and the humerus consists primarily of a large depression known as the trochlear notch in the proximal end of the ulna which receives the distal end of the humerus, or trochlea. The proximal end of the ulna, which forms the proximal side of the trochlear notch, is called the olecranon. The triceps muscle, which extends the forearm, attaches at its lower end to the olecranon.

One of the most common fractures of the elbow involves the olecranon. In the most typical fracture pattern, the olecranon is severed from the rest of the ulna along the bottom of the trochlear notch. Such fractures are often difficult to treat because the powerful muscles attached to the olecranon tend to pull it away from the rest of the ulna and rotate it around the trochlea. This displacement of the olecranon fragment must be reduced and stabilized to allow the fracture to heal.

Numerous techniques have been developed to reduce and stabilize olecranon fractures. For instance, U.S. Pat. No. 3,716,050 describes a metal plate that is used to secure olecranon fractures. Although such plates can provide effective reduction and stabilization, they are difficult to install because of the extensive dissection required to expose the large section of the ulna where the plate attaches. Moreover, the plate eliminates so much of the load on the bone that decalcification can result, leading to weakness after the plate is removed.

Another common treatment makes use of a lag screw installed through the proximal end of the olecranon and extending into the medullary canal of the ulna. Because the threaded region of a lag screw engages the hard cortical bone surrounding the medullary canal, the screw tightens rather suddenly as it starts to engage the bone. Selecting a screw with the proper length and thread diameter so that the screw threads tighten just as the proper compression is applied to the olecranon fragment is often difficult. Moreover, if the threads have not tightened adequately when the fragment is properly compressed, the screw may gradually back out.

In order to address the problem of sudden tightening that occurs with lag screws extending into the medullary canal, shorter cancellous screws have been tried for treatment of olecranon fractures. Such screws do not extend into the medullary canal, but rather engage the softer cancellous bone found in the proximal end of the ulna. The soft cancellous bone allows the depth of the screw to be set as necessary to obtain compression of the olecranon fragment without the problem of the screw being too loose or not fitting in far enough. However, because of their length, short screws do not provide adequate resistance to the torque applied to the olecranon as the forearm is extended.

U.S. Pat. No. 3,763,855 describes a device that can be used to repair olecranon fractures and overcomes some of the difficulties of thread engagement presented by lag screws. In particular, a long threaded medullary pin is provided that is fed down the medullary canal of the ulna. The pin threads into a cortical fixation unit that is installed through the side of the ulna distal to the fracture. Because the fixation unit passes through the cortical bone, it is rigidly held in place. However, installation of the device requires holes to be drilled in the bone at two different locations. It can also be difficult to locate the hole in the fixation unit with the end of the pin.

In yet another treatment method, a pair of stiff wires, known as Kirschner wires, are driven through the olecranon into the ulna. The Kirschner wires essentially nail the fracture together. The trailing ends of the wires are bent into U-shaped heads which are driven into the olecranon to capture one end of a tension band. The tension band loops from the proximal end of the olecranon under the ulna and through a hole formed in the ulna on the distal side of the fracture. The tension band keeps the fractured bone segments from separating and the Kirschner wires prevent lateral shifting and torsional rotation. Use of Kirschner wires is a relatively complex procedure and requires a second hole in the bone for the tension band. Moreover, it can be difficult to obtain proper compression with the tension band and the Kirschner wires sometimes back out.

Due to limitations and problems with the existing devices and methods for repair of olecranon fractures, it is an object of the present invention to provide a simple and reliable method and device to treat fractures of the olecranon.

It is another object of the present invention to provide a screw for use in treatment of fractures of the olecranon that does not rely on threads engaged in the bone surrounding the medullary canal.

One more object of the present invention is to provide a method and device for treating olecranon fractures that requires minimal bone access.

Yet another object of the present invention is to provide a method and device for treating olecranon fractures that imparts adequate longitudinal and rotational stability to the olecranon fragment.

SUMMARY OF THE INVENTION

The present invention is a method for repairing fractures of the olecranon including creating a hole in the proximal end of the ulna, where the hole extends from the proximal end of the ulna to the fracture to define a first region, and from the fracture to the proximal end of the medullary canal to define a second region. A screw is selected having a cancellous section and a medullary section extending from the cancellous section. The cancellous section includes a threaded region adjacent the medullary section and the medullary section is adapted to fit into the medullary canal of the ulna. The medullary section is installed into the hole up to the threaded region and the screw is then rotated to drive the threaded region into the hole until the threaded region engages the cancellous bone surrounding the hole in the second region and the medullary section extends substantially into the medullary canal.

The present invention also includes a bone screw for use in treating olecranon fractures in the ulna. The screw is installed in a hole extending from the proximal end of the ulna to the medullary canal and includes an elongate cancellous section adapted to fit into the hole and extend substantially from a trailing end near the proximal end of the ulna to a leading end near the medullary canal. The cancellous section also includes a threaded region adjacent the leading end. An elongate unthreaded medullary section extends from the leading end of the cancellous section and is adapted to project substantially into the medullary canal of the ulna.

Many other features, advantages and additional objects of the present invention will become manifest to those versed in the art upon making reference to the detailed description which follows and the accompanying sheet of drawings in which preferred embodiments incorporating the principles of this invention are disclosed as illustrative examples only.

DETAILED DESCRIPTION OF THE PREFERRED EMBODIMENT

Figure 1:
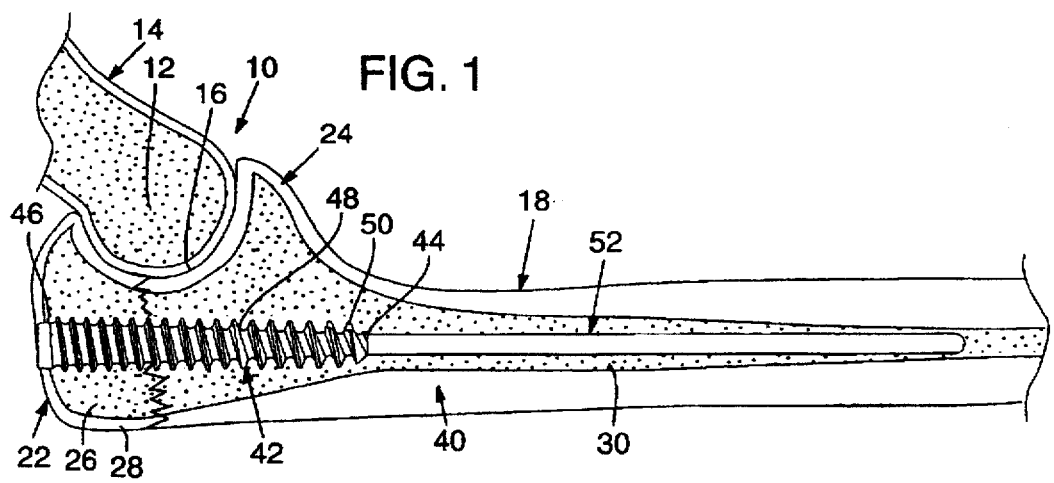
FIG. 1 is a sectional view through an elbow joint showing the structure and placement of a screw constructed according to the present invention.

An elbow is shown generally at 10 in FIG. 1. Elbow 10 includes the distal end or trochlea 12 of humerus 14. Trochlea 12 is received in a trochlear notch 16 in the proximal end of ulna 18. The proximal and distal sides of trochlear notch 20 are formed by olecranon 22 and coronoid process 24, respectively. The proximal end of ulna 18, including the olecranon and coronoid process, consists essentially of cancellous bone 26 surrounded by a shell of cortical bone 28. Distal to the coronoid process, the ulna consists of a shell of cortical bone surrounding a medullary canal 30. In a relatively common fracture of the elbow, the olecranon is severed from the rest of the ulna along the bottom of the trochlear notch. A typical fracture line is shown at 32 in FIG. 1.

Also shown in FIG. 1 is a screw 40 constructed according to the present invention. Screw 40 includes a cancellous section 42 with a leading end 44 and a trailing end 46 and a threaded region 48. A notch 50 is provided in threaded region 48 near leading end 44 to help the threads cut into the bone as the screw is driven in. In the preferred embodiment, threaded region 48 extends over the entire cancellous section and is constructed with variable pitch as described in U.S. patent application Ser. No. 08/506,469, which is hereby incorporated by reference. As described in that patent application, the variable pitch threads draw the bone fragments together as the screw is installed, eliminating the need for a head to create compression.

Projecting from leading end 44 is a medullary section 52 that extends into the medullary canal. The diameter of medullary section 52 is typically somewhat smaller than the inside diameter of the medullary canal. In particular, the leading extension in the preferred embodiment is unthreaded, cylindrical and has a diameter of approximately 3 millimeters. Because the diameter of the medullary canal can vary from 3.5–5 millimeters, the leading portion fits closely within the canal.

It is important that medullary section 52 be of sufficient length to prevent the olecranon fragment from rotating up and back under the pull of the triceps muscles. Typical lengths would range from 25–80 millimeters, with approximately 45–50 being preferred. Moreover, although medullary section 52 preferably unthreaded, it may be desirable to thread the leading portion for some applications.

To install the screw, the surgeon reduces the fracture as necessary to position the olecranon in its proper location. Next, a hole is drilled through the proximal end of the olecranon along the axis of the ulna and extending substantially to the proximal end of the medullary canal. The medullary section is then installed in the hole and pushed in until the threaded region reaches the olecranon. The screw is then screwed in until the trailing end of the cancellous section is beneath the surface of the bone. The compression provided by the threaded region prevents the olecranon from pulling way from the bone in an axial direction, while the length of the screw prevents the torque from the triceps muscles from rotating the fragment up and back.

Figure 2:
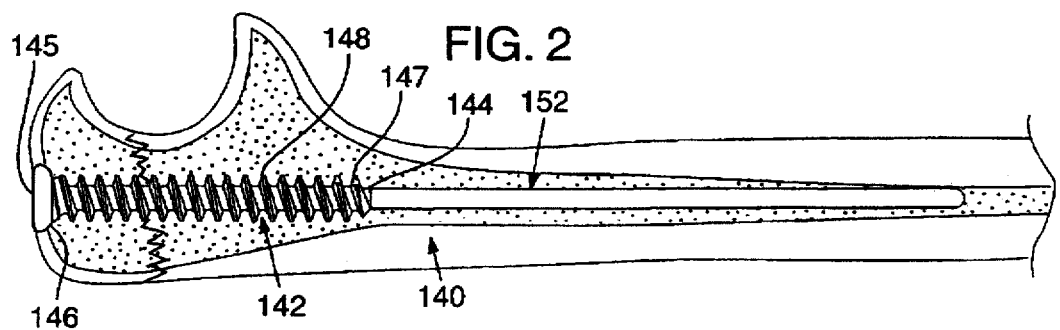
FIG. 2 is a sectional view through an ulna showing the structure and placement of a screw according to an alternative embodiment of the present invention.

An alternative embodiment of a screw according to the present invention is shown at 140 in FIG. 2. Screw 140 includes a cancellous section 142 with a leading end 144, a trailing end 146 and a threaded region 148. A head 145 may be provided at trailing end 146. Threaded region 148 includes constant pitch threads with a notch 147 near leading end 146 to facilitate installation of the screw. As with the first embodiment, screw 140 includes a medullary section 152 which projects from the leading end of the threaded portion.

Since screw 140 does not generate compression as it is driven in, as per screw 40, it is suitable for use where the olecranon is already sufficiently reduced against the rest of the ulna. It can also be used by providing a larger hole in the olecranon to allow the threads to pass freely, thereby allowing head 145 to generate the compression as per a typical lag screw.

Figure 3:
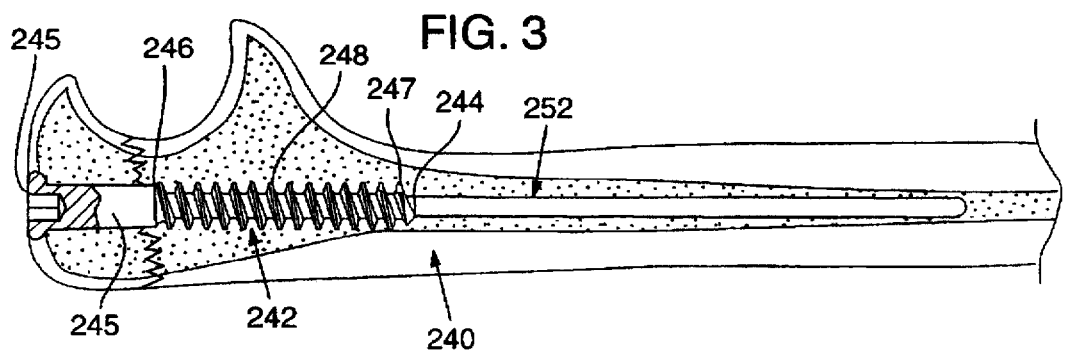
FIG. 3 is a sectional view through the ulna of FIG. 2 showing a second alternative embodiment of a screw according to the present invention.

Another alternative embodiment of a screw according to the present invention is shown generally at 240 in FIG. 3. Screw 240 includes a cancellous section 242 with a leading end 244, a trailing end 246 and a threaded region 248. A notch 247 is formed in threaded region 248 near the leading end 244. An unthreaded medullary section 252 extends from leading end 244. The principle difference over screw 140 is the provision in screw 240 of an unthreaded trailing region 254 disposed between a head 245 and threaded region 248. This allows screw 240 to generate compression without the need to bore a larger hole in the olecranon.

It will now be clear that an improvement in this art has been provided which accomplishes the objectives set forth above. While the invention has been disclosed in its preferred form, it is to be understood that the specific embodiments which have been depicted and described are not to be considered in a limited sense because there may be other forms which should also be construed to come within the scope of the appended claims.

I claim:

1. A method for repairing olecranon fractures in the ulna comprising the steps of:

creating a hole in the proximal end of the ulna, the hole extending from the proximal end of the ulna to the fracture to define a first region, and from the fracture to the proximal end of the medullary canal to define a second region;

selecting a screw having a cancellous section end a medullary section extending from a leading end of the cancellous section to a leading end of the screw, where the cancellous section include a threaded region adjacent the medullary section and the medullary section is adapted to fit into the medullary canal of the ulna, the threaded region being provided with a larger outside diameter than the diameter of the hole in the second region;

installing the medullary section into the hole up to the threaded region; and rotating the screw to drive the threaded region into the hole until the threaded region engages the cancellous bone surrounding the hole in the second region, end the medullary section extends from the second region substantially into the medullary canal, where the medullary section is chosen to have a diameter along its entire length that is less than the corresponding diameter of the medullary canal into which the medullary section is adapted to fit.

2. The method of claim 1 further comprising the step of choosing a screw with an unthreaded medullary section.

3. The method of claim 1 futher comprising the step of choosing a screw with a fully threaded cancellous section.

4. The method of claim 3 further comprising the step of choosing a screw where the pitch of the threads in the cancellous section is larger toward the medullary section and smaller in the opposite direction.

5. The method of claim 1 further comprising the step of choosing a screw where the threaded region is adapted to be substantially coextensive with the second region and the cancellous section includes an unthreaded region adapted to be substantially coextensive with the first region when the screw is installed in the hole.

6. The method of claim 1, wherein the medullary section is chosen to have a constant diameter along its length.

7. A method for repairing a fracture in a metaphysis at a first end of a long bone having a medullary canal comprising the steps of:

selecting a screw having a cancellous section and a medullary section extending from a leading end of the cancellous section to a leading end of the screw, where the cancellous section includes a threaded region adjacent the medullary section and the medullary section is adapted to fit into the medullary canal of the bone;

inserting the medullary section into the bone up to the threaded region of the screw, where the medullary section is inserted from the fast end of the bone through metaphysis toward the medullary canal; and rotating the screw to drive the threaded region into the bone until the threaded region engages the cancellous bone in a distal portion of the metaphysis between the fracture and the medullary canal, and the medullary section extends from the distal portion of the metaphysis substantially into the medullary canal, where the medullary section is chosen to have a diameter along its entire length that is less than the corresponding diameter of the medullary canal into which the medullary section is adapted to fit.

8. The method of claim 7, wherein the threaded region extends over substantially all of the cancellous section.

9. The method of claim 8, wherein the cancellous section includes a head at the trailing end adapted to compress against the first end of the bone.

10. The method of claim 8, wherein the threaded region has larger pitch near the leading end and smaller pitch toward the trailing end.

11. The method of claim 10, wherein the threaded region has an outside diameter that is larger near the trailing end and smaller near the leading end.

12. The method of claim 11, wherein the outside diameter of the threaded region near the trailing end is at least equal to the largest diameter of any portion of the screw.

13. The method of claim 7, wherein the cancellous section includes an unthreaded region near the trailing end and a head at the trailing end adapted to compress against the first end of the bone.

14. The method of claim 7, wherein the medullary section is 2–4 millimeters in diameter.

15. The method of claim 7, wherein the medullary section is 23–80 millimeters long.

16. The method of claim 7, wherein the medullary section has a constant diameter along its length.

* * * * *